United States Patent [19]

Cumberland

[11] Patent Number: 4,888,841
[45] Date of Patent: Dec. 26, 1989

[54] METHOD AND APPARATUS FOR MOLDING SHOE INSERTS

[75] Inventor: Glenn W. Cumberland, Mt. Pleasant, Mich.

[73] Assignee: Foot Technology, Inc., St. Louis, Mo.

[21] Appl. No.: 47,657

[22] Filed: May 8, 1987

[51] Int. Cl.$^4$ .................... A43D 89/00; A43B 13/38
[52] U.S. Cl. ................................ 12/38; 12/142 N; 12/146 M; 128/595
[58] Field of Search .............. 12/142 N, 146 M, 38, 12/21; 128/80 DB, 779, 595; 264/220, 222, 223, DIG. 30; 425/2, 129 S

[56] References Cited

U.S. PATENT DOCUMENTS

| | | | |
|---|---|---|---|
| 2,330,978 | 10/1943 | Klein | 12/146 M |
| 2,955,326 | 10/1960 | Murray | 12/142 N |
| 2,973,529 | 3/1961 | Silverman | 128/595 |
| 3,355,753 | 12/1967 | Lagana | 12/142 N |
| 4,520,581 | 6/1985 | Irwin et al. | 128/595 |
| 4,669,142 | 6/1987 | Meyer | 12/146 M |

FOREIGN PATENT DOCUMENTS

| | | | |
|---|---|---|---|
| 165104 | 12/1921 | United Kingdom | 12/38 |
| 167473 | 5/1922 | United Kingdom | 12/38 |

Primary Examiner—Steven N. Meyers
Attorney, Agent, or Firm—Merchant, Gould, Smith, Edell, Welter & Schmidt

[57] ABSTRACT

A method and apparatus are provided for relatively convenient and efficient production of custom molded inserts for shoes. The apparatus utilizes a molding pillow arrangement, upon which a user stands during use. The molding pillow arrangement has a composite construction including a first resilient layer, a middle resilient layer and a bottom support layer. The bottom support layer preferably includes a generic arch curve therein. The upper resilient layer is formed from a relatively soft foam, and thus molds around a user's feet. The middle layer is resilient, but relatively hard by comparison to the upper layer. The middle layer provides for a relatively firm cushion underneath the user's foot, facilitating contouring of a molded insert to the bottom of the user's foot. Preferably, at least the upper cushion portion of the molding pillow arrangement comprises left and right cushions, independently moldable with respect to a user's left and right feet. A preferred insert construction for use in association with the method and apparatus is provided.

11 Claims, 3 Drawing Sheets

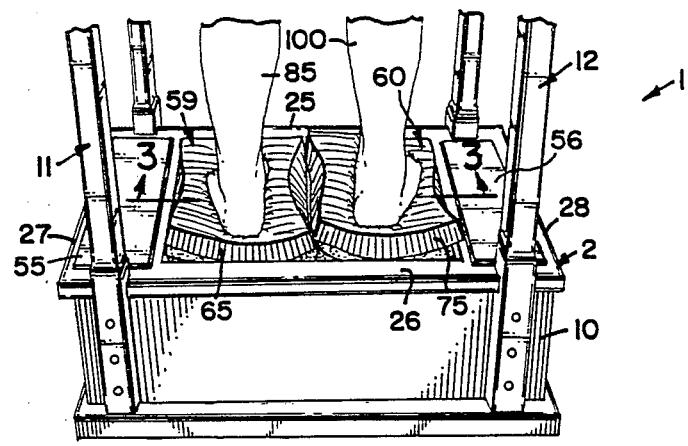
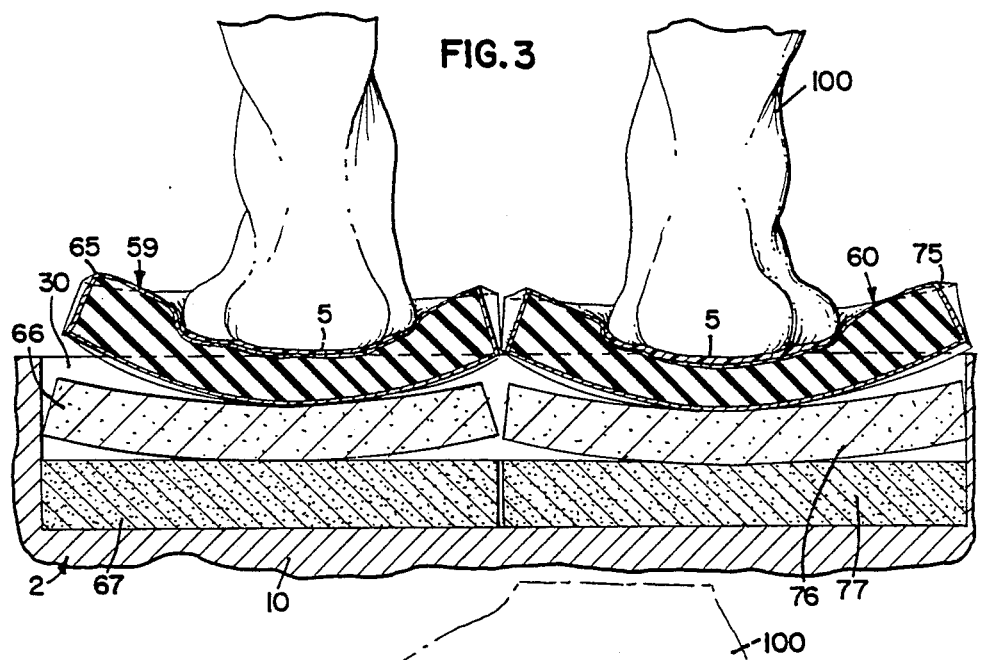
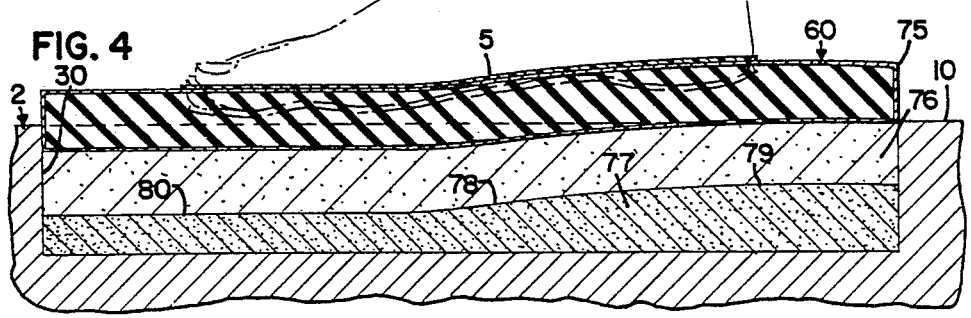

METHOD AND APPARATUS FOR MOLDING SHOE INSERTS

FIELD OF THE INVENTION

The present invention relates to insoles and in particular to custom insoles for support and cushioning of a user's feet. The invention specifically relates to a method and apparatus for molding such insoles.

BACKGROUND OF THE INVENTION

Activities which concern locomotion of the human body, such as walking, running and involvement in various athletic activities, place stress on the bones and joints of the leg and foot. These stresses can be quite great, and can be harmful if the bones and joints of the foot are not supported properly.

One method of providing support for the foot is through the utilization of standardized or universal insole cushions and arch supports. While these do provide some support and comfort, due to their standardization and lack of customization they are inadequate for many uses. In particular, since the shape of feet vary greatly, as well as people's weight, weight distribution, leg structure and knee structure, standardized inserts and arch supports lack universal utility with optimized results.

Custom insole systems have been developed. An example is the FOOT TECH Custom Insole system developed by Foot Technology, Inc., the assignee of the present invention. Generally, the FOOT TECH system involves the construction of a mold of the user's foot. The mold is typically kept by the manufacturer and is used to custom mold shoe inserts. Such inserts may include, for example, a custom molded arch support, a heel section and a toe section.

Such custom methods and arrangements have been available for a considerable period of time and have been highly effective. However, a problem with such methods is that they are generally inconvenient to the end user and are relatively expensive. Thus, while they suit the professional athlete fairly well, they are generally unacceptable to many lay persons.

More convenient and inexpensive custom molding systems have been developed. One such arrangement is known as the CONFORM'ABLE system from SIDAS, apparently available through Bio-Dynamics, Inc. of Concord, N.H. 03301. This system is generally used for mountaineering-type footwear and ski-wear. The insole is a thermal-molded product. The product is heated until it becomes moldable, and then it is stepped upon by the user. As the insole cools, it forms to the user's feet. Generally, the system involves placing the insole upon a foam molding pad having a built-up arch support portion. The molding pad permits the heated insert to conform to the user's feet. The arch support molds an arch curve into the insert. An advantage to this arrangement is that the inserts can be formed in a matter of minutes; for example, in a shoe store or a sporting goods store.

Another insole molding system is available from Peterson Laboratories of Lake Placid, N.Y. Peterson offers a BIOCOMFORT system in which an insert is molded, upon a pillow, in the shoe store. The Peterson pillow is designed such that a forward portion of the foot rests upon very little cushion, during molding, whereas the heel portion of the foot is on an apparently soft, considerably built-up pillow. Peterson also has offered a related BIOTHOTIC system in which an impression of the foot is molded in a low density polyethylene sheet. The sheet material, after molding, apparently is used as a core for a shoe insert, which is later manufactured.

These and similar methods are directed to the development of a method for conveniently, relatively rapidly and inexpensively forming a custom insert for shoes. The methods generally involve attempts to solve the two interrelated problems of:

1. Providing for preparation of a custom insert in a relatively short period of time, at low expense; and
2. Providing of a molding method by which a properly supportive insert is formed.

Various insert materials have been developed, to aid in molding and operation of the finished product.

In general, while available methods approach desirable low-cost, easily made custom inserts, there has been need for improvement in the general areas outlined above. The present invention in particular addresses these problems.

OBJECTS OF THE INVENTION

Therefore, the objects of the present invention are: to provide a method and apparatus for molding shoe inserts; to provide a preferred insert for relatively easy and inexpensive molding by such a method and apparatus; to provide a method of molding shoe inserts involving the utilization of a multi-layer molding support for the user; to provide a preferred such a molding support comprising an upper layer of a first resiliency and a lower layer of a second resiliency; to provide such an apparatus wherein the upper resilient layer comprises a soft foam and the second lower layer comprises a more firm foam; to provide such an arrangement wherein a user steps upon a left set of cushions with one foot and a right set of cushions with another foot during typical use; to provide such an arrangement wherein the upper soft foam layers are sufficiently soft to substantially wrap around a user's foot during molding; to provide such a method and arrangement wherein the lower, more firm, layer provides a substantially firm yet cushioned support underneath the more soft layer, for efficient molding; to provide a particularly effective stand apparatus for use in implementation of such a method; and, to provide such a method, apparatus and insert which are relatively inexpensive to produce and use, and which are particularly well adapted for the proposed uses thereof. Other objects and advantages of this invention will become apparent from the following descriptions, taken in connection with the accompanying drawings, wherein are set forth by way of illustration and example certain embodiments of the present invention.

SUMMARY OF THE INVENTION

A method is provided for forming custom insoles. The method generally involves the use of a molding pillow arrangement and moldable inserts.

In a typical operation, the molding pillow arrangement is oriented so that it can be stepped upon by a user. Preferably, the pillow arrangement comprises first and second composite pillow members or portions, each having two cushion or pillow layers and a rigid support layer.

For the preferred embodiment, each of the two pillow members has a rigid lower support formed from styrofoam or the like. The lower support preferably has a constant lateral cross-section and a rear to front downward curve. The downward curve generally corresponds to a generic arch curve and conveniently provides for a molded insole with a raised heel utilizable, comfortably, in shoes with or without raised heels.

For the preferred embodiment two cushion layers are positioned above the lower support layer. The resiliency and/or firmness of the two cushion layers preferably differ from one another, in a preferred manner. Specifically, the uppermost cushion layer is softer than the central or lower cushion layer. For the preferred embodiment, each of the cushions is of a constant cross-section both laterally and from front-to-rear. In use they are supported with a curved shape, as a result of resting upon the lower curved rigid support portion.

As a result of having a relatively soft structure, the upper cushion or layer operably wraps substantially around the foot of a person who stands thereon. This causes deformation of a moldable insert positioned between the user's foot and the cushion, to comfortably wrap around the foot of the user and mold the insert into conformity with the shape of the user's foot. In particular, this arrangement provides for a relatively deep heel portion and a well-defined arch support section.

As previously described, the central or lower cushion layer of the preferred embodiment is firmer or of greater resiliency than the upper layer. This relatively firm layer cushions a user standing upon the pillow arrangement and generates a good molding of the bottom of the insert to the bottom of the user's feet, particularly in the arch and toe areas. The relatively firm construction of the lower cushion layer facilitates weight distribution.

In the preferred embodiment the upper and lower cushion layers are separable from one another. As a result, a technician can slip his or her hand, or an implement, between the two layers during a molding operation. In this manner the position of a foot of a person standing upon the cushions can be adjusted. Further a molded shape of an insert can be modified, enhanced and controlled.

As previously indicated, for the preferred embodiment the molding pillow arrangement is separated into first and second sides or halves. Generally, the user stands upon the arrangement with one foot on one half and the other foot on the other half. At least the upper cushion, and preferably both the upper and the central cushions, are disjointed from one another along the line separating the two halves. As a result, the two upper cushions are free to form and mold about each of the user's feet, independently.

In the preferred embodiment, for typical use the pillow arrangement is oriented within a stand. The stand includes arm rests and a knee-positioning mechanism. The knee positioning mechanism can be utilized to selectively orient a person standing upon the pillows, before molding is undertaken. The arm supports help the user to securely stand upon the yielding cushions.

The preferred knee positioning mechanism is a cushioned bar which is adjustable vertically, and also toward and away from a user. This system is advantageous since it can be rapidly adjusted by a technician, and can comfortably accommodate a variety of users.

In a typical use, the left and right molding cushions are positioned within a recess in the stand. The user stands upon the pillows and his or her feet are appropriately oriented upon the pillows. The user then steps off of the pillows and a heated, deformable, insole insert is placed on each of the pillow members.

The user then steps upon the inserts, repositioning his or her feet in the previously determined preferred orientation according to markers on the pillows and through use of the knee-positioning mechanism. The user remains standing upon the moldable inserts until molding is completed. This generally takes two to five minutes. The user then steps off of the molded inserts, the inserts are trimmed as necessary and are then readily usable by insertion into the user's shoes. During the molding operation, the technician may insert a hand or object between the cushions to selectively adjust positioning of the foot or molding of the insert.

Preferred inserts according to the present invention are composite structures and may be of varying types. An often preferred composite includes a lower thermoplastic layer which is soft, and flexible but which retains its molded shape at and near room temperature and which becomes relatively moldable when heated. The next layer may preferably include a rigid material such as a piece of polyvinylchloride plastic arch support which can be molded after having been heated. The next layer above the moldable portion(s) is preferably a cushioning or shock-absorbing layer, generally comprising a polymeric cushion or the like. Above the shock absorbing layer, and typically adjacent the user's feet, is located a top member comprising nylon or the like which permits the user's foot to breathe and which can readily absorb moisture and provide a comfortable surface. Other cushion layers may be utilized, as desired. Further, while rigid arch supports may be prescribed, they are not required in all instances.

In some applications of the present invention the composite insole insert may include means providing for the mounting of a medical support therein. This can be accomplished by providing for separability between several of the composite layers, and by providing an insert positionable therein.

The drawings constitute a part of this specification and include exemplary embodiments of the invention, while illustrating various objects and features thereof. In some instances relative component sizes or material thicknesses may be shown exaggerated, for clarity.

BRIEF DESCRIPTION OF THE DRAWINGS

FIG. 2 is a fragmentary rear perspective view of the apparatus shown in FIG. 1, with a user standing thereon.

FIG. 3 is an enlarged fragmentary cross-sectional view taken generally along line 3—3, FIG. 2.

FIG. 4 is an enlarged fragmentary side cross-sectional view taken generally from the orientation of line 4—4, FIG. 1, prior to a user stepping thereon; phantom lines generally indicating deformation from a user's foot also shown in phantom lines.

DETAILED DESCRIPTION OF THE PREFERRED EMBODIMENT

As required, detailed embodiments of the present invention are disclosed herein. It is to be understood that the disclosed embodiments are merely exemplary of the invention, which may be embodied in various forms. Therefore, specific structural and functional details disclosed herein are not to be interpreted as limiting, but rather as a basis for the claims and as a representative basis for teaching one skilled in the art to variously employ the present invention in virtually any appropriately detailed structure.

Figure 1:
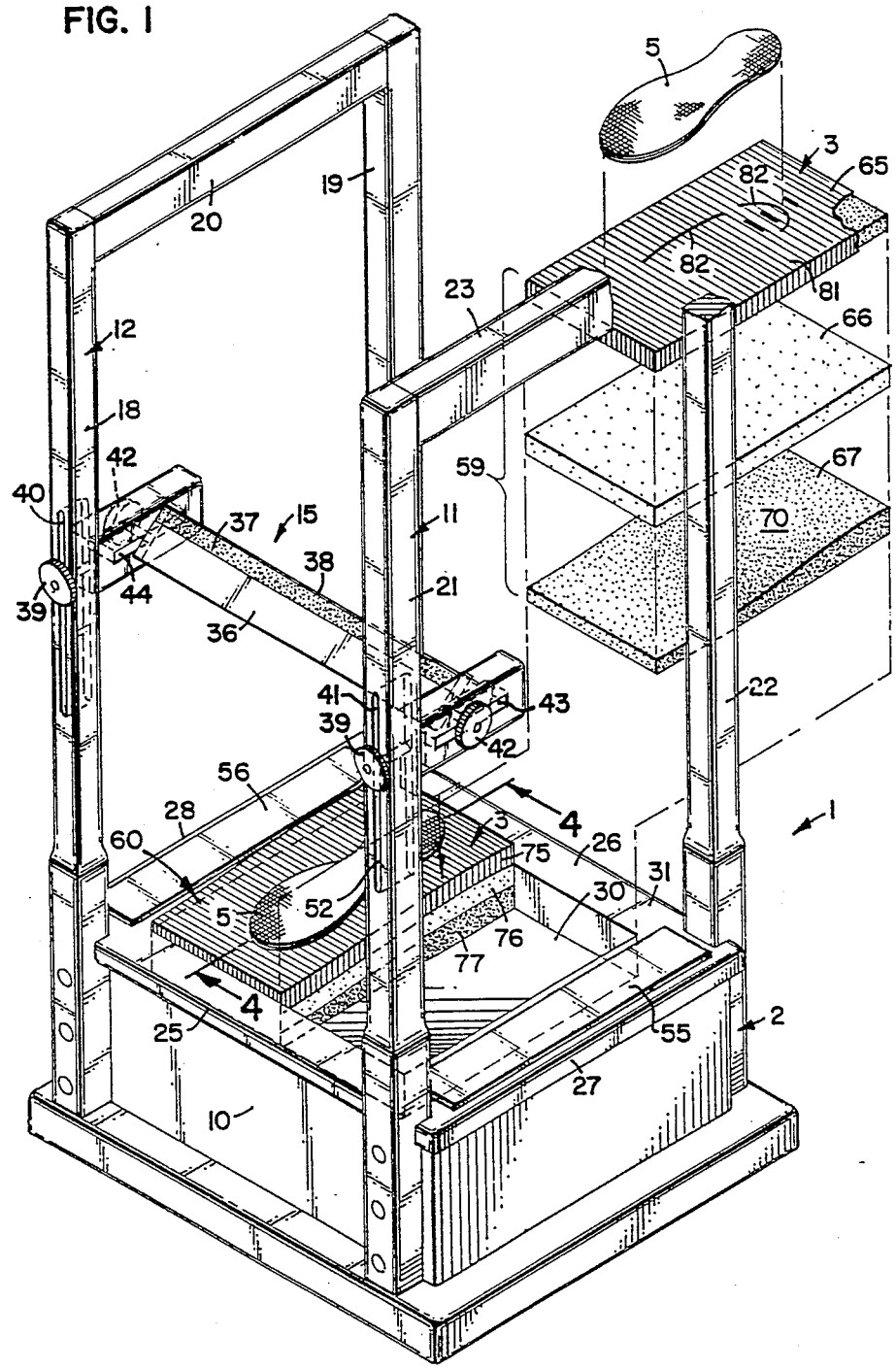
FIG. 1 is a fragmentary, exploded perspective view of an apparatus according to the present invention, with portions broken away to show detail.

The reference numeral 1, FIG. 1, generally designates an overall apparatus utilizable in association with the principles of the present invention. The apparatus 1 comprises a stand 2 having a molding pillow arrangement 3 therein. Specific advantages, according to the present invention, are obtained from the particular molding pillow arrangement 3 described and shown.

In FIG. 1, apparatus 1 is shown in a typical orientation for use in molding insoles. In FIG. 1, composite insoles 5 are shown oriented for molding. According to the present invention, the insoles 5 are heated, until moldable, and are positioned on the pillow arrangement 3, as shown. A user then stands upon the insoles 5 molding same. The user typically remains standing upon the insoles 5 until the insoles 5 sufficiently cool to a molded state in which they will remain.

Referring again to FIG. 1, stand 2 includes a base or pedestal portion 10, left and right handrail extensions 11 and 12 respectively, and a knee positioning mechanism 15.

The right handrail extension 12 comprises first and second upward extensions 18 and 19 with hand rail 20 extending therebetween. Preferably hand rail 20 is supported at a convenient height for use in steadying a person standing upon pillow arrangement 3. Generally handrail 20 is typically positioned at a height between hip and waist level for most users.

Similarly, left handrail extension 11 comprises upward extensions 21 and 22 and hand rail 23.

Base 10 includes a front portion 25, a rear portion 26 and left and right side portions 27 and 28 respectively. The base 10 includes an upper recess 30, defined by border or curb 31, in which molding pillow arrangement 3 is received during use. Recess 30 insures secure positioning of members of the molding pillow arrangement 3, inhibiting their unintended movement during use.

Knee positioning system 15 includes an adjustable bar 36. The bar 36 includes a cushion 37 thereon, which is pressed against a user's knees during a molding operation. The cushion 37 has an outer covering 38 of nylon or the like, for convenience.

The bar 36 is vertically positionable and is movable toward and away from a user. Also, the bar 36 is rotationally adjustable. For the preferred embodiment illustrated in FIG. 1, the bar 36 is vertically adjustable, by means of clamps 39, in slots 40 and 41. The bar 36 can be moved toward and away from a person standing within apparatus 1, by means of adjustment of clamps 42 in slots 43 and 44. Rotational adjustment is also facilitated by clamps 42.

The mechanism for adjusting knee positioning is preferred over conventional systems for numerous reasons. First, it can be adjusted forward and back. Secondly, it can be rapidly adjusted. Also, both knees can be quickly adjusted and are comfortably supported. Adjustment in positioning of a user's knees can be used to selectively orient the position of and weight distribution on a user's feet, as a user stands upon molding pillow arrangements 3. As a result, a selected, reproducible, position for a user can be set, prior to placing a moldable insert underneath a user's feet. This will be further described below.

Referring again to FIG. 1, non-slip mats 55 and 56 are shown mounted on sides 27 and 28. During operation of apparatus 1 should it become necessary for a user to straddle recess 30, non-slip pads 55 and 56 facilitate security and safety.

Referring to FIG. 1, molding pillow arrangement 3 for the preferred embodiment comprises first and second pillow members 59 and 60. Members 59 and 60 comprise a left pillow member 59 and a right pillow member 60. For the preferred embodiment the two pillow members 59 and 60 are independent of one another, both being positioned in recess 30.

Pillow members 59 and 60, for the preferred embodiment, are composite members with substantial advantages being obtainable from the composite arrangement. Referring to FIG. 1, member 59 is shown comprising first, second and third layers 65, 66 and 67 respectively. Layer 67 is a relatively rigid base having an upper surface 70. Member 67 has a substantially constant lateral cross-section, FIG. 3. However, it has a downwardly slanted curve therein, from rear to front, which supports the contour of the longitudinal arch areas with respect to heel height.

In FIG. 4, a side cross-sectional view of pillow member 60 is shown. Pillow member 60 includes first, second and third layers 75, 76 and 77 respectively. Member 77 is a rigid layer substantially identical to member 67, FIG. 1. Arch curve 78 is viewable in FIG. 4 sloping downwardly from a rear heal portion 79 to a front toe portion 80 of rigid member 77. For the preferred embodiment, curve 78 approximates an arch curve for a person having a shoe with a slightly raised heel. Typically the heel area is raised over the toe area a total of between about one-quarter and three-quarter inches, and preferably is raised about one-half inch.

Preferably, members 67 and 77 are easily formable from a relatively inexpensive, available material. For the preferred embodiment, members 67 and 77 are formed from styrofoam. As a result, members 67 and 77 do not substantially compress when stood upon by a user. Preferred members 67 and 77 may be cut from a single rectangular piece of styrofoam, with cutting between side edges simultaneously forming both pieces. As a result of being formed from relatively inexpensive styrofoam, members 67 and 77 can be readily discarded and/or replaced as necessary.

Referring again to FIG. 1, layers 65 and 66 are compressible layers. That is, each of layers 65 and 66 compress when they are stood upon by a user. Preferably each is formed from a foam material such as a polyurethane foam rubber or the like. Layers 65 and 75 are formed from a relatively soft foam with advantages resulting therefrom, as will be discussed in more detail below. Members 66 and 76, the central or lower members, are formed from a foam which is harder or firmer than layers 65 and 75. The provision of a pillow member having upper and lower resilient layers of different resiliency, with the upper layer being softer, yields particular advantages according to the present invention.

Referring to FIG. 1, upper layer 65 includes an outer covering 81 formed from nylon or the like. An analogous covering may be used on the lower layer 66. The covering provides an easily cleanable covering for the cushion(s). Further, it may be readily marked or imprinted, as for example with markings 82 utilizable to selectively position the user's foot and the insert 5. Another advantage to covering 81 is that it protects foam 65 from damage and further provides a protective coating for the hot moldable insert 5.

Advantages obtained from the relatively soft upper layer of foam will be understood by reference to FIGS. 2, 3 and 4. Referring to FIG. 2, upper layers 65 and 75 are shown laterally spaced from one another, with a user 85 standing thereon. Since the foam of the upper layers is relatively soft, the user's feet will substantially sink therein, with the foam wrapping substantially up and around the user's foot. Layer 65 can wrap around the user's left foot, and independently layer 75 can wrap around the user's right foot, since the two foam members 65 and 75 are completely separate from one another. When deformable inserts are placed between the user's feet and cushions 65 and 75, the inserts will be readily molded up around the user's foot, as a result of the soft foam. Thus, a relatively deep heel portion will be formed in the insert, as well as a well-defined arch portion and an edge line wrapping upwardly around the user's foot.

As previously explained for the preferred embodiment, the middle layers 66, 76 of the cushions 59 and 60 are also compressible, but are formed from a foam which is somewhat harder than the upper layer. This forms a compressible base upon which a user can stand. The relatively high resiliency of middle layers 66, 76 leads to some resistance to the wrapping around illustrated by upper layers 65, 75. Thus, the middle layers 66, 76 firmly push upwardly against the bottom of the user's feet. This pushes the upper cushion 65 and 75, and any deformable insert positionable between cushions 65 and 75 and the user's feet, up toward the bottom of the user's feet. The result is a molding of contours into the molded insole which conform well to the bottom of the user's feet. An advantage to the firmer cushion is that it facilitates good weight distribution during molding.

As a result of the two different resiliencies of cushions used for each composite pillow member, and the utilization of an upper relatively soft cushion member, an effective mold is provided for the user's feet. The mold is readily usable in association with a moldable insert placed upon upper surfaces of pillows 59 and 60, and is quickly prepared for reuse. The upper, soft, layer forms a relatively deep heel cup, and good arch wrapping and a side edge to the molded insert. The firmer lower cushion supports the weight of the user while generating contouring in the bottom of the insert.

It is noted that while the preferred embodiment has upper and lower cushions (65 and 66; or, 75 and 76) which are completely separable, the upper and lower cushions could be attached or be integral with one another. However, advantages result from their separability or at least partial separability since, during molding, a technician can insert a hand or object between the two layers to effect or adjust molding, or the position of a user's foot.

Figure 5:
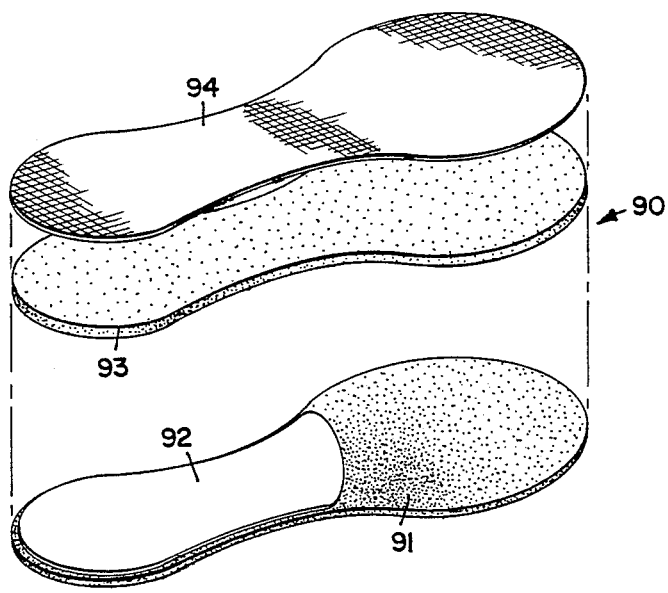
FIG. 5 is an enlarged exploded view of a composite insert usable according to the present invention in the molding process thereof.

Referring to FIG. 5, an insole insert 90 utilizable, as shown for insert 5, FIG. 1, in association with the present invention is illustrated. Insert 90 is a composite member having: a lower thermoplastic layer 91; an arch and heel support member 92; a cushion layer 93; and, an upper protective layer 94. While a variety of composite structures might be utilized in association with the principles of the present invention, the structure of FIG. 5 is convenient and preferred in many uses.

Referring again to FIG. 5, lower layer 91 is a thermoplastic layer which may be readily molded in an apparatus according to the present invention. Layer 91 preferably comprises a soft plastic material which has substantial memory at room temperature and typical use temperatures, to provide contouring for the insert 90. When the material from which layer 91 is formed is heated substantially, as for example in a convection oven at 250° F., for several minutes, it becomes pliable and moldable. A preferred thermoplastic material for layer 91 is VINYLPLEX a polyvinyl chloride material available in a strip form from Alpha Plastics of St. Louis, Mich. 49990. The strips of VINYLPLEX are made from GEON 87438, a B.F. Goodrich polyvinylchloride product.

In some instances a fairly rigid arch support may be prescribed. The preferred insert portion 92, FIG. 5, is a somewhat triangularly shaped piece of material which is not as soft or flexible as thermal plastic layer 91 but which is deformable and moldable, when heated, to form an arch support and heel cup. Preferably insert 92, as suggested, is formed from material which at room temperatures and typical use temperatures is sufficiently rigid to provide substantial support. A preferred material for insert 92 is a plastic material such as a polyvinylchloride which, when heated along with thermoplastic layer 91, becomes sufficiently pliable to be moldable to conform to a user's heel and arch and further which readily cools to a molded, relatively rigid, construction.

For the insert illustrated in FIG. 5, layer 93 comprises a shock absorbing layer of foam or the like. Preferably layer 93 is formed from a relatively durable synthetic material. It may be of a variety of thicknesses, depending upon the cushioning effect desired for the insole insert.

Upper layer 94, FIG. 5, comprises a protective layer of a material such as nylon or the like which can be readily cleaned, which will be comfortable for a user within that user's shoes, and preferably which will absorb moisture draining same away from the user's feet and permitting the user's feet to breathe somewhat.

In a typical application, layers such as layers 91,92,93 and 94 are formed into a composite insert such as insert 5, FIG. 1. The insert is then heated, until it becomes moldable, in a convection oven or the like. Preferably, the materials are chosen such that insert 5 becomes moldable when heated in a convection oven at about 250° F. for about two to five minutes. Thus, the insert will be warm, but handlable.

Referring to FIG. 4, the heated insert 5 is positioned on top of an appropriate cushion, such as cushion 75. When a user's foot 100 is positioned thereon, under the weight of the user's foot the insert 5 will be depressed into, and is molded by, the upper relatively soft cushion 75 in association with the lower relatively hard cushion 76. Arch curve 78 provides for a raised heel in the molded insert 5, thus providing an arrangement comfortable with either flat shoes or shoes with raised heels.

Figure 6:
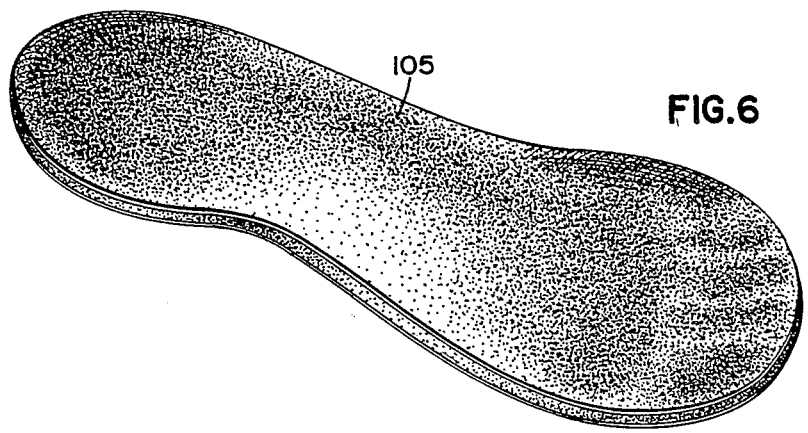
FIG. 6 is an enlarged perspective view of a molded insert made according to the present invention.

Referring to FIG. 6, a molded composite insert 105 is depicted.

Inserts having a variety of composite structures may be utilized in association with many of the principles of the present method, although the arrangement of FIG.

5 having two moldable layers 91 and 92 of different resiliency offers advantages in some applications. Generally, the layers may be formed into a single unit by use of adhesives or the like. These units can be readily formed into left foot and right foot units, if desired. In FIG. 6 a molded left foot unit is depicted.

Figure 7:
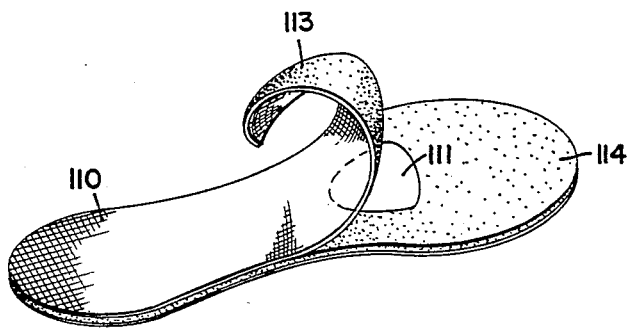
FIG. 7 is a perspective view of an insert according to the present invention made with a medical split therein, phantom lines indicating portions out of view.

In some applications of the present invention, it may be desirable to provide a medical support such as a metatarsal support within the insert. Referring to FIG. 7, an insert 110 is shown having a medical support 111 positioned therein. The arrangement illustrated in FIG. 7 will be referred to herein as a "medical split". The medical split shown comprises a composite structure 110 having an upper portion 113 and a lower portion 114. Although the heel portions of members 113 and 114 are glued or adhered to one another, front portions thereof are separable or split, so that insert 111 can be easily positioned therein, either before or after molding. In this manner, the insert 111 can be selectively positioned for the particular patient involved. If desired, layer 113 can be attached to layer 114 by means of adhesive, after medical support 111 is positioned. This medical support 111 offers distinct advantages not generally available from conventional system 5.

Typical operation of the present method will be understood by reference to FIGS. 1-4. Referring to FIG. 1, for a preferred application apparatus 1 is prepared with first and second molding pillows 59 and 60 positioned therein, and with the arch curves slanted downwardly or toward the front portion 25 of base 10. Recess 30 helps retain the cushions 65, 66, 75 and 76 in position.

Markings 82 are provided on upper surfaces of relatively soft pillows 65 and 75. The user stands upon pillows 65 and 75 with his or her feet appropriately positioned with respect to markings 82, to achieve proper alignment with the downward arch curve. The markings can be utilized to accommodate, for example, appropriate positioning of persons with feet of varying sizes. The user's knees are placed into association with cushion 37 and bar 36. The bar 36 is selectively oriented to position the user's legs, knees and feet in a preferred orientation. During this process, the user can steady himself or herself through the use of horizontal rails 20 and 23.

Detail is not provided herein with respect to selection of an orientation of the user's feet, knees and legs. Theories and hypotheses with respect to this may vary. Further, the particular orientation selected is not critical to application of the present invention as a wide variety of orientations can be accommodated.

After appropriate positioning of knee support bar 36, the user can then either step out of apparatus 1 or, if desired, can straddle pillow members 59 and 60 by stepping upon strips 55 and 56. Heated, prepared, inserts 5 are then positioned appropriately upon upper pillows 65 and 75, with respect to markings 82, for that selected user. Prior to being placed upon pillows 65 and 75, inserts 5 will have been appropriately heated as to become moldable.

The user then steps downwardly upon moldable inserts 5, standing thereon and supporting themselves by rails 23 and 20, if necessary, while the molding process is completed. The markings 82 and knee positioning mechanism 15 can be used to reproduce the earlier selected position. Referring to FIGS. 2, 3 and 4, the relatively soft upper cushions 65 and 70, and relatively firm lower cushions 66 and 76 provide for a desirable molding of the insert 5 with respect to the user's feet, especially in forming arch portions and heel portions. After several minutes, operable inserts 5 will have sufficiently cooled to form inserts, such as insert 105, FIG. 6, having contours conforming to the user's feet. The user then steps off of the apparatus 1, and the molded inserts are removed and trimmed as necessary. The inserts may then be placed in the user's shoes, as custom insole supports and cushions.

If desired, an insert involving a medical split may be used. Under such circumstances, the medical support can be positioned either before or after molding, as desired.

In some applications, the custom molded insert can be used to form a base or core around which a more built-up insert is provided. For example, a molded insert such as insert 105 may be used to form the core of a larger insert utilized in a ski boot or the like. This could be accomplished, for example, by taking molded insert 105 and adding cushioning or space-filling material to an underside thereof, to build-up a permanent or semi-permanent insert for a ski boot or the like.

Referring to FIG. 3, for the preferred embodiment described and shown, the lower support members 67 and 77 are separate from one another, but are substantially identical. It will be understood that the two lower relatively rigid members 67 and 77 could be made integral with respect to one another, and further could be directly formed within base 10. However, the styrofoam arrangement described and shown is preferred and members 67 and 77 can be removed and replaced independently from one another, as desired.

Generally, middle layers 66 and 67, of the preferred embodiment, are completely independent from one another. As a result, they may wrap somewhat around a user's foot, while providing firm support for the upper layer 65 and 75 respectively. While in FIG. 3 little such deformation is exhibited, it may be substantial under the certain circumstances, depending in part upon the weight and size of the user. It will generally be advantageous to provide members 66 and 76 separate from one another in an apparatus according to the present invention.

According to the present invention, it is generally a requirement that cushions 65 and 75, the upper cushions, be either completely separate from one another or joined in such a manner that they may independently deform as shown in FIG. 2 to wrap around a user's foot.

A variety of weights and resiliencies of cushions may be utilized in association with the principles of the present invention. Generally what is required is a cushion material for the upper cushion which is sufficiently soft as to provide for the pronounced wrapping effect illustrated in FIG. 3 and described herein. Further, generally what is required for the middle layers is a resilient material which is harder than the upper layers and provides for a good firm effective lower support.

A preferred foam material for both layers is a polyurethane foam. An example is TEMPER FOAM® available from KGM (Kees Goebel Medical) of Hamilton, Ohio 45011. The preferred upper layer is pink TEMPER FOAM®, a polyurethane foam assigned KGM product code T-38. The density of such material is generally about 6.4 pounds per cubic foot with a tensile strength of about 22 psi, an ultimate elongation of 218%, a ball rebound resilience value of 3.6%, an indentation force deflection (25% IFD value) of 156 IFD-Newtons, and a compression set $C_t$ at 50% of 1%.

A preferred middle layer, also formed from TEMPER FOAM®, is a polyurethane foam, available from KGM under product code T-41 with a density of about 6.4 pounds per cubic foot, a tensile strength of about 36 psi, an ultimate elongation of about 200%, a ball rebound resilience value of about 4.6% and an indentation force deflection (25% IFD value) of about 223 IFD-Newtons. For the preferred embodiment both the upper layers 65 and 75 and the middle layers 66 and 76 are about one inch thick.

While a variety of foams may be used as the upper and lower layers, generally preferred foam for the upper layer has: a tensile strength of 14–30 psi; and a ball rebound resilience value of 3.0–4.0%. Preferred foam for the lower layer has: a tensile strength of 31–40 psi; and, a ball rebound resilience valve of 4.1–5.0%.

If a user's feet are too large for apparatus 1, FIG. 1, the molding pillows 59 and 60 can be removed therefrom and placed upon the floor. Cushion extensions may then be placed in association with the members 59 and 60, extending the length to handle a relatively large foot and insert.

If the user is a person who has trouble standing, pillow arrangements such as 59 and 60 may be utilized in association with a variety of support arrangements for the user, including ones wherein considerable support is provided for the user, leading to relatively little downward force or weight upon the feet. It will be understood that under such circumstances, variations in weight thickness and firmness of foam may be desireable.

As previously suggested, advantages result from having upper and lower foam layers (ex. 65 and 66) which are separable from one another, so a technicians hand or an object can be inserted therebetween during molding. While further advantages are derived for such a system wherein the foam layers have different resiliencies as described, advantage from separability of lower and upper layers results regardles of the relative firmness of the layers.

It is to be understood that while certain embodiments of the present invention have been illustrated and described, the invention is not to be limited to the specific forms or arrangement of parts herein described and shown.

What is claimed and desired to be secured by Letters Patent is as follows:

1. A support apparatus for use in molding an insert placed thereon to a user's foot, said support apparatus comprising:
   (a) an upper resilient layer of relatively soft foam material capable of substantially molding about a foot of a person placed thereon; and,
   (b) a lower resilient layer of foam material; said lower resilient layer being substantially firmer than said upper resilient layer and being capable of providing a support substantially contoured to a bottom of a foot placed on said support apparatus;
      (i) said upper and lower resilient layers: being separable from one another, enabling insertion of a member therebetween; and, being constructed and arranged in a manner facilitating molding of said upper resilient layer, about a user's foot at least partially independently of molding of said lower resilient layer.

2. A support apparatus according to claim 1 including:
   (a) a base member positioned underneath said lower resilient layer; said base member being substantially rigid and including an arch curve with a raised heel.

3. A molding pillow arrangement for use in molding an insert placed thereon to a user's feet; said pillow arrangement comprising:
   (a) a first foot support pillow member having an upper resilient layer of relatively soft foam material capable of substantially molding about a first foot of a person placed thereon; said first foot support pillow member having a lower resilient layer of foam material, said lower resilient layer being substantially firmer than said upper resilient layer and being capable of providing a support substantially contoured to a bottom of a first foot of a person placed on said first foot support pillow member;
      (i) said upper and lower resilient layers of said first pillow: being separable from one another, enabling insertion of a member therebetween; and, being constructed and arranged in a manner facilitating molding of said upper resilient layer, about a user's foot, at least partially independently of molding of said lower resilient layer;
   (b) a second foot support pillow member having an upper resilient layer of relatively soft foam material capable of substantially molding about a second foot of a person placed thereon; said second foot support pillow member having a lower resilient layer of foam material, said lower resilient layer being substantially firmer than said upper resilient layer and being capable of providing a support substantially contoured to a bottom of the second foot of a person placed on said second foot support pillow member;
      (i) said upper and lower resilient layers of said second pillow: being separable from one another, enabling insertion of a member therebetween; and, being constructed and arranged in a manner facilitating molding of said upper resilient layer, about a user's foot, at least partially independently of molding of said lower resilient layer;
   (c) said first foot support pillow member upper resilient layer being constructed and arranged to be moldable about the person's first foot substantially independently of molding of the second foot support pillow member upper resilient layer about the person's second foot.

4. The molding pillow arrangement of claim 3 wherein each upper resilient layer comprises a polyurethane foam layer having a tensile strength of between about 14 and 30 psi, a ball rebound resilience value of between about 3.0 and 4.0%, and wherein each upper resilient layer is at least about one inch thick.

5. The molding pillow arrangement of claim 4 wherein said lower resilient layer of each support pillow member comprises a polyurethane foam layer having a tensile strength of between about 31 and 40 psi and a ball rebound resilience value of between about 4.1 and 5.0%.

6. The molding pillow arrangement of claim 3 wherein:
   (a) said first foot support pillow member includes a lower rigid base portion having an arch curve and a raised heel; and
   (b) said second foot support pillow member includes a lower rigid base portion having an arch curve and a raised heel.

7. An apparatus for use in preparing custom molded shoe inserts; said apparatus comprising:
   (a) a support apparatus having a base portion, an arm rail portion and a knee positioning mechanism;
      (i) said base portion including a pillow mechanism-receiving recess therein;
   (b) a molding pillow mechanism positioned within said receiving recess and comprising a left pillow arrangement and a right pillow arrangement; each of said left and right pillow arrangements including:
      (i) an upper resilient layer of relatively soft foam material capable of substantially molding about a foot of a person placed thereon; and
      (ii) a lower resilient layer of foam material beneath each upper resilient layer; said lower resilient layer; being substantially firmer than said associated upper resilient layer and being capable of providing a support substantially contoured to a bottom of a foot placed on said pillow arrangement; and,
      (iii) said associated upper and lower resilient layers: being separable from one another, enabling insertion of a member therebetween; and, being constructed and arranged in a manner facilitating molding of said upper resilient layer, about a user's foot, at least partially independently of molding of said lower resilient layer.

8. An apparatus according to claim 7 wherein said knee positioning mechanism includes a knee positioning bar vertically and horizontally adjustable for selective engagement with a user's knees.

9. An apparatus according to claim 8 including:
   (a) a base member positioned underneath each lower resilient layer; said base members each being substantially rigid and having an arch curve with a raised heel.

10. The apparatus of claim 9 wherein each upper resilient layer comprises a polyurethane foam layer having a tensile strength of between about 14 and 30 psi, a ball rebound resilience value of between about 3.0 and 4.0%, and a thickness of at least about one inch.

11. The apparatus of claim 10 wherein said lower resilient layer of each support pillow member comprises a polyurethane foam layer having a tensile strength of between about 31 and 40 psi and a ball rebound resilience value of between about 4.1 and 5.0%.

* * * * *